United States Patent [19]

Davis et al.

[11] 4,042,618

[45] Aug. 16, 1977

[54] AROMATIC SULFONATES

[75] Inventors: Gerald A. Davis, Charlotte, N.C.; Robert W. Stackman, Morristown, N.J.

[73] Assignee: Celanese Corporation, New York, N.Y.

[21] Appl. No.: 263,086

[22] Filed: June 15, 1972

Related U.S. Application Data

[60] Division of Ser. No. 27,942, April 13, 1970, Pat. No. 3,706,712, which is a continuation-in-part of Ser. No. 833,729, June 16, 1969, abandoned.

[51] Int. Cl.$^2$ ............................................. C07C 143/42
[52] U.S. Cl. ................................. 260/470; 260/507 R; 260/512 C; 260/512 R
[58] Field of Search ........... 260/507 R, 512 R, 512 C, 260/470

[56] References Cited

U.S. PATENT DOCUMENTS

| | | | |
|---|---|---|---|
| 3,393,221 | 7/1968 | Boehmke et al. | 260/512 R |
| 3,700,721 | 10/1972 | Price et al. | 260/507 R |
| 3,712,919 | 1/1973 | Juelke et al. | 260/512 R |

FOREIGN PATENT DOCUMENTS 43-26000   1968   Japan

*Primary Examiner*—C. Davis
*Attorney, Agent, or Firm*—Pamela D. Kasa; Roderick B. Macleod

[57] ABSTRACT

Aromatic sulfonates and fiber and film forming polymers containing these sulfonates, the sulfonates being represented by the general formula:

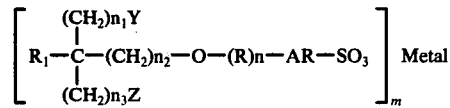

wherein $R_1$ represents either hydrogen or an alkyl radical containing from 1 to about 6 carbon atoms; $n$, $n_1$, $n_2$ and $n_3$ each independently represent an integer from 0 to about 6, and $n_1 + n_2 + n_3$ is equal to or greater than 2 if Y and Z both are hydroxy; Y and Z are selected independently from the class consisting of hydroxy, carboxy, and alkoxycarbonyl, the alkoxy portion of which contains from 1 to about 6 carbon atoms; Ar represents a divalent aromatic radical which may be substituted or unsubstituted; $m$ is an integer equal to the valency of the metal; and R represents a divalent radical, with the proviso that where $n$ is O and Ar is phenylene, the metal is lithium.

6 Claims, No Drawings

AROMATIC SULFONATES

This application is a division of application Ser. No. 27,942, filed Apr. 13, 1970 now U.S. Pat. No. 3,706,712 which in turn is a continuation-in-part of application Ser. No. 833,729, filed June 16, 1969, now abandoned.

The invention relates to novel aromatic sulfonates, compositions of said aromatic sulfonates with film- and fiber-forming, linear synthetic polyesters, and shaped articles produced therefrom. More particularly, the invention is directed to novel aromatic sulfonates which are capable of being incorporated into fiber-forming, linear condensation polyesters which in turn can be shaped into articles such as films, fibers, and the like, having an affinity for basic dyes.

Successful methods have been suggested in the past to improve the dyeability of shaped articles, such as films, fibers, and fabrics made from linear synthetic polyesters wherein basic dyes are utilized to provide brighter colors and to permit cross dyeing of the shaped articles. These methods utilize the technique of incorporating sulfonated compounds into linear synthetic polyesters to provide basic dyeable compositions. A typical procedure for the preparation of modified synthetic polyester is represented by U.S. Pat. No. 3,018,272, which describes the process of producing basic dyeable polyesters having incorporated therein as copolymers sulfonated monomers. Similarly, Japanese Patent 26000/68 cites the preparation of dyeable copolyesters by adding prior to the completion of polymerization at least one compound represented by the following general formulae:

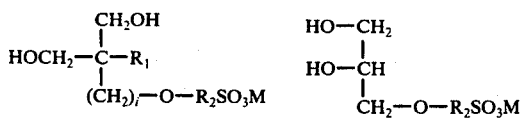

wherein $R_1$ is either hydrogen or an alkyl group; $R_2$ is either an alkylene or a phenylene group; M is hydrogen or an alkali metal; and $i$ is either 0 or 1. In selecting such monomers or basic dye sensitizing units, it is necessary to consider a wide variety of related properties, including those inherent in the additive and those which develop during the course of polymerization or use. Additive properties would include melting or decomposition point, boiling point, solubility in the polymer, reactivity toward copolymerization, effectiveness as a chain terminator, thermal stability, color and the like. In addition to retention of normal properties of the polymer and shaped articles made therefrom, examples of properties which develop during the course of polymerization or use would include polymer color, availability of dye sites, high polymer molecular weight, dyeability with basic dyes, hue of dyed article, uniformity of dye uptake, and heat-, light- and wash-fastness of the dyed article.

It is therefore an object of the present invention to provide a novel class of aromatic sulfonates.

Another object is to provide shaped articles produced from fiber-forming linear condensation polyesters modified with a novel class of aromatic sulfonates, the shaped articles having an affinity for basic dyes.

Still another object of the present invention is to provide a process for the production of fiber-forming, linear condensation polyesters modified with a novel class of aromatic sulfonates from which polyester shaped articles having an affinity for basic dyes can be prepared.

These and other objects will become apparent in the course of the specification and claims which follow.

A novel class of aromatic sulfonates contemplated by this invention may be represented by the general formula:

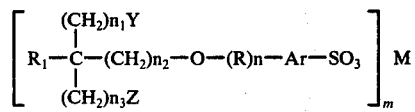

wherein $R_1$ represents either hydrogen or an alkyl radical containing from 1 to about 6 carbon atoms; $n$, $n_1$, $n_2$, and $n_3$ each independently represent an integer from 0 to about 6, and $n_1 + n_2 + n_3$ is equal to or greater than 2 if Y and Z both are hydroxy; Y and Z are selected independently from the class consisting of hydroxy, carboxy, and alkoxycarbonyl, the alkoxy portion of which contains from 1 to about 6 carbon atoms; Ar represents a divalent aromatic radical which may be substituted or unsubstituted; M represents any metal capable of forming salts of aromatic sulfonic acids; $m$ is an integer equal to the valency of the metal M; and R represents a divalent radical selected from the group consisting of alkylene, cycloalkylene, aralkylene, alkarylene, arylene,

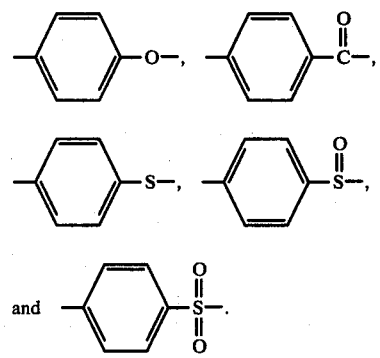

A preferred embodiment of the present invention may be described in terms of the general formula given hereinabove, wherein $R_1$ is hydrogen; $n_1 + n_2 + n_3$ is either 0 or 2; Y and Z are the same and are either hydroxy or carboxy; Ar is selected from the group consisting of 1,4-phenylene, 2,7-naphthylene, and 1,5-naphthylene; R is alylene; and M is either lithium or sodium and most preferably lithium. The lithium salts are preferred in that linear condensation polyesters modified with the lithium salt of the aromatic sulfonates of this invention dye to the darkest shade and hence a lower amount of lithium salt additive may be used to achieve a preselected depth of dyeing.

A further class of aromatic sulfonates contemplated by this invention may be represented by the general formula:

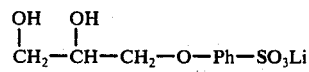

wherein Ph is phenylene, either substituted or unsubstituted.

The preferred compounds of this invention are:

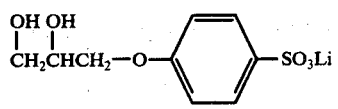 3-(4-Lithiosulfophenoxy)-1,2-propanediol

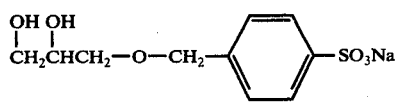 3-(4-Sodiosulfobenzyloxy)-1,2-propanediol

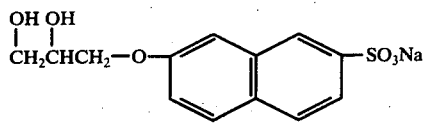 3-(7-Sodiosulfo-2-naphthoxy)-1,2-propanediol

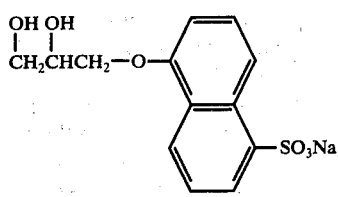 3-(5-Sodiosulfo-1-naphthoxy)-1,2-propanediol

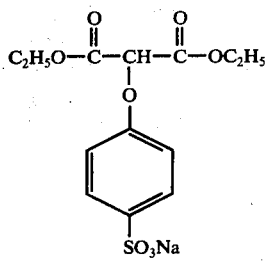 Diethyl 2-(4-Sodiosulfophenoxy)-malonate

The novel classes of aromatic sulfonates as disclosed above can be prepared by a variety of methods, depending in part upon the structures of the desired compounds. Without attempting to present an exhaustive summary, the following descriptions are representative of the types of reactions which may be employed to obtain the novel aromatic sulfonates of this invention.

1. The reaction of either (a) a metallic aryloxide with an alkyl halide, or (b) a metallic alkoxide with an aralkyl halide. In general, a metallosulfo moiety will be a part of the metallic aryloxide or aralkyl halide, while the metallic alkoxide and alkyl halide will be substituted in such a manner as to provide, after reaction, the compounds of the present invention.

2. The reaction of an aromatic alcohol with an aliphatic carbonate, with the aromatic alcohol containing the metallosulfo moiety. The aliphatic carbonate will be substituted as described in (1) above for the metallic alkoxide and alkyl halide.

3. The reaction of an aromatic alcohol with an aliphatic epoxide. The aromatic alcohol will contain the metallosulfo moiety, while the aliphatic epoxide will be substituted as described in (1) above for the metallic alkoxide and alkyl halide.

It should be apparent that in each of the above types of reactions the reaction may be carried out without the metallosulfo (or sulfo) moiety being a part of any reactant. The metallosulfo moiety may be introduced after reaction by sulfonation, followed by neutralization. This procedure, however, is not preferred because the conditions of sulfonation give rise to competing side reactions which are not desirable. Furthermore, sulfonation or aromatic rings yields a mixture of several isomers which either must be used as such or given extensive purification in order to isolate the desired pure compound.

Although not as applicable as the preceding three types of reactions, a fourth type may be mentioned: the addition of an aromatic alcohol to an alkene. As with the preceding types, the alkene will be substituted in such a manner as to provide, after reaction, the compounds of the present invention. In general, the aromatic alcohol may contain the metallosulfo moiety. Within the limitations already indicated, the metallosulfo moiety may be introduced after reaction by sulfonation and neutralization.

Incorporation of the aromatic sulfonates of the present invention into linear synthetic polyesters provides dye sites for basic dyes. It is usually desirable to use at least about 0.5 weight percent of aromatic sulfonate based on the weight of polymer. Incorporation of less than 0.5 weight percent usually results in polymers having only a relatively low affinity for basic dyes. Polymers containing about 10 weight percent of aromatic sulfonate have a very high affinity of basic dyes. Higher concentrations will not lead to appreciable increases in basic dyeability and in general may unduly affect tenacity in the shaped articles. Concentrations of aromatic sulfonates in the range of 1 to 5 weight percent are preferred.

Although the emphasis has been on the use of pure compounds, the use of mixtures of aromatic sulfonates also is contemplated by the present invention. For example, it already has been pointed out that sulfonation of an aromatic nucleus yields a mixture of ortho, meta, and para isomers, even though the para isomer usually predominates. Depending upon the particular compounds involved, it may be necessary or desirable to use such a mixture without purification. Furthermore, it may on occasion be either necessary or desirable to use a mixture of previously purified compounds. Such a mixture could be either a mixture of different metal salts of the same compound or a mixture of two structurally different compounds, the cations (metal portion) of which may be the same or different. Thus, while the use of single, pure aromatic sulfonates usually is preferred, the use of such mixtures as outlined above may be either necessary or desirable to achieve a proper balance of such properties as depth of dye uptake and lightfastness of the dyed article.

Especially desirable results may be afforded by a combination of selected aromatic sulfonates including members of the class comprehended by this invention, either with or without a dye opener ingredient copolycondensed therewith. In these selected instances, very small amounts of one of the aromatic sulfonates, e.g., as little as 0.025 weight percent, may be utilized in accordance with this invention to confer the desired level of basic dyeability together with other necessary properties of both the fiber and dyed article, such as tenacity, elongation, lightfastness, colorfastness, etc. An example is the combination of 3-(4-lithiosulfophenoxy)-1,2-propanediol with 5-lithiosulfoisophthalic acid or the dimethyl ester thereof, wherein the molar ratio of the components of said combination varies within the polyester from about 0.005 to about 200, the weight percent of said combination in the polyester being in the range of about 0.5 to about 5.

As indicated hereinabove, lithium is the most preferred cation or metal portion of the aromatic sulfonates of the present invention, since lithium aromatic sulfonates surprisingly impart deeper dyeability to linear synthetic polyesters than other alkali metal aromatic sulfonates. It also has been found that the use of the lithium salt may avoid or minimize spinning difficulties with sulfonates of poor solubility in the polyester medium. Thus, as shown by Examples XXXIV and XXXV, the use of lithium eliminates the formation of small particles which are insoluble in the polyester, which particles plug sand filters and spinnerette holes, causing spinning interruptions (failing filaments and slow holes), and which also have a limiting effect on draw ratio by causing frequent filament breaks at drawing. Fine particles passing through the filters introduce heterogeneous regions into the spun yarn and therefore may modify drawing characteristics and adversely affect physical properties of the drawn yarn. Thus the use of lithium allows attainment of longer pack lives, reduced pack pressures and hence improved pump performance, more efficient spinning as a result of fewer spinning interruptions, higher draw ratios which contribute, at least in part, to higher tenacities in drawn fibers and filaments, and improved drawn yarn uniformity. Although incorporation of e.g. the sodium salt of 3-(4-sulfophenoxy)-1,2-propanediol into poly(ethylene terephthalate) as contemplated by Japanese Patent 26000/68 does result in a basic dyeable copolyester, there are present in the resultant copolyester insoluble particles, 10–60 microns in size. These insoluble particles, which are a major problem as outlined hereinbefore, constitute about 0.8% by weight of the copolyester. The particles themselves are about 25% by weight unpolymerized 3-(4-sodiosulfophenoxy)-1,2-propanediol, with the remainder being what is believed to be a low molecular weight oligomer having the following structure:

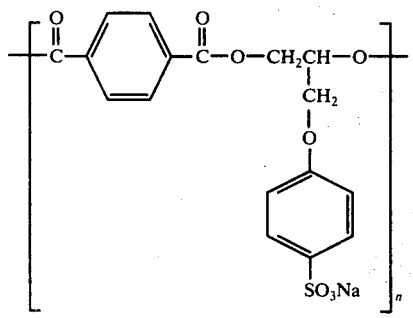

A better appreciation of the significance of the aforementioned particles may be had by referring to the drawings. FIG. 1 is a photomicrograph (magnification, 250X) of fibers obtained from copolymer containing 3-(4-sodiosulfophenoxy)-1,2-propanediol, wherein said particles are readily observed. FIG. 2 is a similar photomicrograph of fibers obtained from polymer containing 3-(4-lithiosulfophenoxy)-1,2-propanediol; the absence of particles resulting from use of the lithium salt in place of the sodium salt is both striking and obvious. Finally, in addition to the foregoing, the use of 3-(4-sodiosulfophenoxy)-1,2-propanediol results in the agglomeration of the titanium dioxide delustrant of the copolyester. The titanium dioxide delustrant is required for the aesthetics of fibers and filaments made from said copolyester. Replacing the sodium salt of 3-(4-sulfophenoxy)-1,2-propanediol with the lithium salt completely eliminates insoluble particles from the copolyester and allows the use of titanium dioxide delustrant without agglomeration of same. Not only are all of the problems associated with said insoluble particles eliminated, but also the amount of sulfonate salt may be reduced significantly while maintaining a level of basic dyeability equivalent to that obtained through the use of the sodium salt.

While an exact explanation for the foregoing phenomenon is not available and without wishing to be bound by theory, it may be postulated that the striking results obtained with lithium derive from the smaller ionic radius and hence increased electronegativity of lithium relative to the ionic radii and electronegativities of its congeners (elements in the same group). By way of illustration, the ionic radius of lithium (about 0.68 A ) is approximately 70% that of the next smallest congener, sodium (ionic radius about 0.98 A ); thus lithium is the most electronegative of the alkali metals. Consequently, it may be rationalized that the increased solubilities of lithium aromatic sulfonates in relatively non-polar solvents (i.e., polyester) relative to other alkali metal aromatic sulfonates is the result of a somewhat more covalent bond between the lithium and a sulfonate oxygen. Furthermore, it may be postulated that exchange between the dye cation and the lithium ion occurs more readily than with the other alkali metal ions because of the relatively small size of the lithium ion, assuming that the availability of dye sites is, in part at least, a function of the ability of the metal ion to diffuse away from the dye site.

The term "linear synthetic polyester" as used herein includes as a preferred class polyester prepared from terephthalic acid or its dialkyl ester and a polymethylene glycol having the formula:

$$HO(CH_2)n_4OH$$

wherein $n_4$ is an integer from 2 to about 8. In this preferred class, the most preferred polyester, poly(ethylene terephthalate), is obtained when $n_4$ is 2. If desired, the polymethylene glycol may be replaced entirely or in part with other glycols, such as 1,4-cyclohexanedimethanol; 1,4-bis-(2-hydroxyethoxy)benzene, and the like; preferably, no more than about 10 percent of the polymethylene glycol will be replaced with another glycol. Additionally, other dicarboxylic acids or their esters, such as adipic acid, succinic acid, isophthalic acid, 1,1,3-trimethyl-5-carboxy-3(p-carboxyphenyl)indane, and the like may be added in amounts up to about 10 weight percent to produce copolyesters.

Various other materials may be present in the reaction mixture. For example, such ester interchange catalysts as salts of calcium, magnesium, manganese, cobalt, zinc, and the like and such polymerization catalysts as antimony trioxide, antiomonic acid, germanium dioxide, stannous oxalate, organo-titanium compounds, and the like, usually will be present. Color inhibitors, such as alkyl or aryl phosphate esters, alkyl or aryl phosphite esters, and the like may be used. In addition, pigments, delustrants such as titanium dioxide or barium carbonate, and other additives may be present.

The yarns or filaments in continuous or staple form produced in accordance with the present invention are suitable for the usual textile applications. They may be employed in the knitting or weaving of all types as well as in the production of non-woven, felt-like products produced by known methods. The physical properties of the modified yarns or filaments closely parallel those of their related non-modified polyester fibers. The modified yarns or filaments differ, however, in that they have a particular sensitivity toward basic dyes. By a "basic dye" is meant a colored cationic organic substance such as those containing sulfonium, oxonium or quaternary ammonium functional groups. Among the basic type which may be applied either to the filaments in continuous or staple form obtained in accordance with the present invention or to fabrics prepared therefrom may be mentioned Victoria Green WB (C.I. Basic Green 4), a dye of the triphenylmethane type having the following chemical structure:

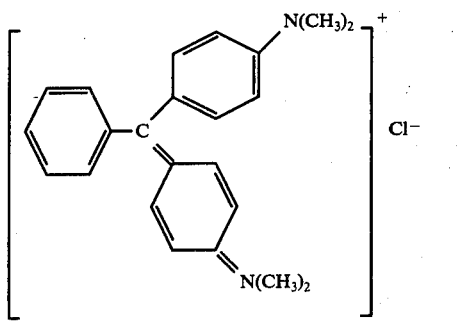

Victoria Pure Blue BO (C.I. Basic Blue 7), a triarylmethane type dye having the following chemical structure:

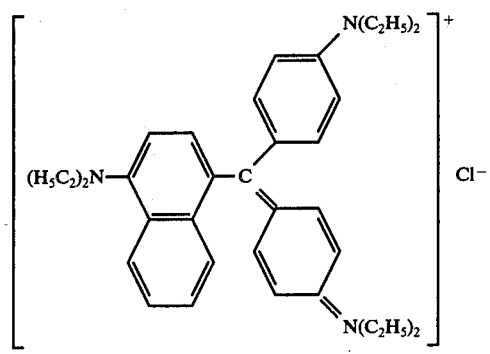

Sevron Blue 5G (C.I. Basic Blue 4), a dye of the oxazine type having the following chemical structure:

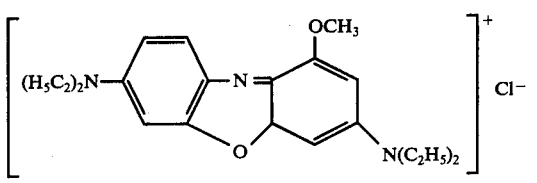

Brilliant Green B (C.I. Basic Green 1), a triphenylmethane type dye having the following chemical structure:

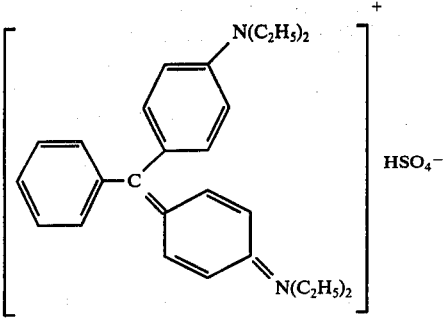

and Rhodamine B (C.I. Basic Violet 10), a dye of the xanthene type having the following chemical structure:

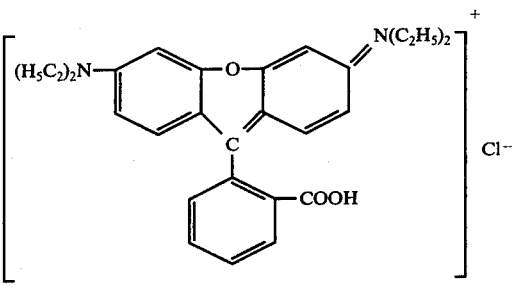

and the like. The dyes are preferably applied from an aqueous solution at a temperature between 80° C and 125° C.

Filaments and films, i.e. shaped structures which have at least one dimension relatively very small and at least one dimension relatively large, are the preferred structures of the present invention. Such structures of the polyester compositions of this invention are permeated uniformly throughout by basic dyes applied from hot aqueous solution. The penetration of dyes is an important characteristic since poor resistance to fading and loss of color through rubbing or abrasion is a known characteristic of structures which retain dye only at their surfaces.

Without intending to limit it in any manner, the following examples will serve to illustrate the invention:

EXAMPLE I

A 12-liter, four-necked round-bottomed flask, fitted with mechanical stirrer, thermometer, reflux condenser, addition funnel, and heating mantle, is charged with 3600 parts of water followed by 417 parts of 97% sodium hydroxide. The mixture is stirred to dissolve the sodium hydroxide. With continued stirring, 2322 parts of p-phenolsulfonic acid, sodium salt, dihydrate is added to the flask. The contents of the flask are warmed to 50°-60° C. By means of the addition funnel, 1105 parts of 3-chloro-1,2-propanediol is added drop-wise to the flask over a two-hour period. The flask then is heated to reflux (103°-106° C) and refluxing continued for about 19 hours. The heat is turned off and the pH of the solution is adjusted to pH 8 by adding 25% aqueous sodium hydroxide solution. The solution is then cooled to 23° C by placing the flask in a cold water-bath and a heavy white precipitate forms upon seeding. A slurry is maintained by vigorous stirring and gradually introduced to a 12-inch perforated basket centrifuge. The flask is rinsed with 600 ml. of 3:1 ethanol-water in order to transfer remaining product into the centrifuge. The solid in the centrifuge is then washed with two 1000-ml. portions of 4:1 ethanol-water. The damp solid is re-dissolved in 6 liters of 3:1 ethanol-water upon heating to 70° C. The solution is then cooled to 23° C to precipitate the product which is isolated by centrifugation and washed once with 1000 ml. of 4:1 ethanol-water. The yield of dry 3-(4-sodiosulfophenoxy)-1,2-propanediol is 1620 parts and is 99.9% pure as determined by the analysis of adjacent hydroxyl groups; the product contains 0.027% chloride. Elemental analysis of the product gives the following results:

|  | %C | %H | %S | %Na |
|---|---|---|---|---|
| Found | 40.75 | 4.21 | 10.94 | 8.17 |
| Calculated | 40.00 | 4.11 | 11.86 | 8.51 |

Thermogravimetric analysis of the product indicates that there is no weight loss at 300° C. The melting point of the product, as determined by differential thermal analysis, is 354° C; a phase transition occurs at 269° C with decomposition occurring at 374° C.

EXAMPLE II

Using the same apparatus as described in Example I, the flask is charged with 4000 parts of water and 1318 parts of potassium hydroxide (85%). The mixture is stirred until a solution is obtained. To the flask then is added 2670 parts of a 65% aqueous solution of p-phenolsulfonic acid, followed by 1100 parts of 3-chloro-1,2-propanediol. The resultant solution is refluxed for about 24 hours. The pH is adjusted to 8 by adding 25% aqueous potassium hydroxide solution. The solution is concentrated by heating under reduced pressure and then is cooled to 20°-25° C by placing the flask in a cold water-bath. Solid precipitates. The solid is isolated by suction filtration and washed three times with 4:1 ethanol-water. The dried product, 3-(4-potassiosulfophenoxy)-1,2-propanediol, is obtained in a yield of 2030 parts and with a purity of 97%, based upon adjacent hydroxyl group analysis; chloride content is 0.03%. Thermal gravimetric analysis of the product shows that there is no weight loss at 300° C.

EXAMPLE III

Using the same apparatus as described in Example I, the flask is charged with 4000 parts of water and 840 parts of lithium hydroxide, monohydrate. The mixture is stirred until a solution is obtained. To the flask then is added 2670 parts of a 65% aqueous solution of p-phenolsulfonic acid, followed by 1100 parts of 3-chloro-1,2-propanediol. The resultant solution is heated at reflux (about 104° C) for about 24 hours. The pH is adjusted to 8 by adding 25% aqueous lithium hydroxide solution. The solution is concentrated by heating under reduced pressure and then is cooled at 20°-25° C by placing the flask in a cold water-bath. Solid precipitates. The solid is isolated by suction filtration and washed three times with 1000 parts of isopropanol. The solid then is reslurried in 9:1 isopropanol-water, filtered, and washed several times with 9:1 isopropanol-water. The isolated product is reslurried, filtered, and washed a second time. The dried product, 3-(4-lithiosulfophenoxy)-1,2-propanediol, is obtained in a yield of 980 parts and with a purity of 99%, based upon adjacent hydroxyl group analysis; the product contains 0.05% chloride.

Elemental analysis of the product gives the following results:

|  | %C | %H | %S | %Li |
|---|---|---|---|---|
| Found | 42.42 | 2.79 | 12.37 | 4.51 |
| Calculated | 42.52 | 2.73 | 12.61 | 4.37 |

Thermogravimetric analysis and analysis by nuclear magnetic resonance give the same results as are obtained with the product of Example I. Differential thermal analysis shows a phase transition at 253° C with the melting point at 353° C.

EXAMPLE IV

A 5-liter, three-necked, round-bottomed reaction flask, fitted with stirrer, reflux condenser, thermometer, and heating mantle is charged with 1800 parts of water, 925 parts of epichlorohydrin, and 2 parts of concentrated sulfuric acid and heated at 75°-80° C for about 20 hours.

Using the same apparatus as described in Example I, the flask is charged with 3500 parts of water, 413 parts of 97% sodium hydroxide, and 2322 parts of p-phenolsulfonic acid, sodium salt, dihydrate and the resulting solution heated to 50°-60° C. By means of the addition funnel, the neutralized epichlorohydrin reaction solution is added dropwise to the flask over a period of about three hours. The resultant solution then is refluxed (103°-106° C) for about 20 hours, then neutralized to pH 8 by adding 50% aqueous sodium hydroxide solution. With continued heating, the reaction solution is concentrated under reduced pressure with about 1 liter water being removed. The concentrated solution is cooled in a cold water-bath to 20°-25° C which results in the precipitation of product. The product is isolated by suction filtration, washed with 4:1 ethanol-water and recrystallized twice from 3:1 ethanol-water. The yield of dry 3-(4-sodiosulfophenoxy)-1,2-propanediol is 1400 parts and is 98% pure as determined by the analysis of adjacent hydroxyl groups; the product also contains 0.15% chloride.

EXAMPLE V

Using the same apparatus as described in Example I, the flask is charged with 2600 parts of water and 459 parts of 97% sodium hydroxide. The mixture is stirred to dissolve the sodium hydroxide. With continued stirring, 2322 parts of p-phenolsulfonic acid, sodium salt, dihydrate is added to the flask, followed by 925 parts of epichlorohydrin. The resulting solution is heated at reflux for about 24 hours. The reaction solution is cooled to 20°-25° C by placing the flask in a cold water-bath and a white precipitate forms upon seeding. The product is worked up as described in Example I. The yield of dry 3-(4-sodiosulfophenoxy)-1,2-propanediol is 1600 parts; the product is 99% pure as determined by adjacent hydroxyl group analysis; chloride content is 0.1%.

EXAMPLE VI

A mixture of 25 parts of 3-(4-lithiosulfophenoxy)-1,2-propanediol, 150 parts of ethanol, and 10 parts of water is heated until a solution is obtained. Similarly, 19 parts of lead acetate trihydrate is dissolved in 25 parts of ethanol. The two solutions are combined, resulting in a white precipitate. The product, the lead salt of 3-(4-sulfophenoxy)-1,2-propanediol, is isolated by filtration, washed with ethanol, and dried.

EXAMPLE VII

The experiment of Example VI is repeated, except that the lead acetate solution is replaced with a solution of 8.8 parts of calcium acetate monohydrate in 50 parts of ethanol and 25 parts of water. Combining the two solutions results in the precipitation of the calcium salt of 3-(4-sulfophenoxy)-1,2-propanediol.

EXAMPLE VIII

Using the apparatus of Example I, the flask is charged with 4500 parts of water and 400 parts of sodium hydroxide; the mixture is stirred until the caustic dissolves. To the flask then is added 2460 parts of 2-naphthol-7-sulfonic acid, sodium salt. The mixture is stirred and heated to 50°-60° C. By means of the addition funnel, 1105 parts of 3-chloro-1,2-propanediol is added drop-wise to the flask over a two-hour period. The reaction solution then is gradually heated to reflux (100°-105° C) and refluxed for about 20 hours. The hot solution is treated with charcoal and filtered while hot through fuller's earth. The filtrate is allowed to cool, resulting in the precipitation of crude product which is isolated by suction filtration. The crude product is dissolved in hot 3:1 ethanol-water, treated with charcoal, and filtered while hot through fuller's earth. The filtrate is allowed to cool. The preceding recrystallization procedure is repeated four times; the product is dried at 100° C in a vacuum oven. The yield of 3-(7-sodiosulfo-2-naphthoxy)-1,2-propanediol is 550 parts. The product is better than 99% pure as determined by adjacent hydroxyl group analysis; chloride content is 0.28%. The product has an uncorrected melting point of 310° C.

EXAMPLE IX

A 5-liter, four-necked, round-bottomed reaction flask, fitted with mechanical stirrer, thermometer, reflux condenser, addition funnel, and heating mantle, is charged with 2500 parts of water and 120 parts of sodium hydroxide and the mixture stirred to dissolve the caustic. To the flask is added 738 parts of 1-naphthol-5-sulfonic acid, sodium salt. Stirring is continued while heating the solution to 50°-60° C. To the flask then is added drop-wise over a two-hour period 332 parts of 3-chloro-1,2-propanediol. The temperature of the reaction solution is gradually increased to reflux (100°-105° C) and refluxing continued for about 20 hours. The hot solution is treated with charcoal, filtered while hot through fuller's earth, and the filtrate cooled to allow precipitation. The product is isolated by suction filtration and washed in hot isopropanol. The product is recrystallized by dissolving in hot 3:1 ethanol-water, treating with charcoal while hot, filtering through fuller's earth, and allowing the filtrate to cool. The product, 3-(5-sodiosulfo-1-naphthoxy)-1,2-propanediol, is isolated by filtration and dried at 110° C under reduced pressure. The yield of 99% pure (as determined by adjacent hydroxyl group analysis) product is 100 parts; the product contains 0.04% chloride. The product has an uncorrected melting point of 375° C (with decomposition).

EXAMPLE X

A 500-ml., four-necked, round-bottomed flask, fitted with mechanical stirrer, thermometer, reflux condenser, addition funnel, and heating mantle, is charged with 261 parts of o-dichlorobenzene and 34.4 parts of p-toluenesulfonic acid, sodium salt. The mixture is heated to 85° C and a small amount of benzoyl peroxide added. Over a 3-hour period, 27 parts of bromine is added drop-wise to the flask. The resultant reaction solution is refluxed for 30 minutes. With continued but reduced heating, the pressure in the vessel is reduced to distill solvent. The residue is taken up in dimethyl sulfoxide and the product, 4-sodiosulfobenzyl bromide, precipitated by adding carbon tetrachloride. The following element analysis is obtained:

|  | % Carbon | % Hydrogen | % Sulfur |
|---|---|---|---|
| Calculated | 30.79 | 2.21 | 11.74 |
| Found | 32.63 | 2.19 | 12.37 |

A 300-ml. beaker is charged with 18.4 parts of glycerin and 1.7 parts of sodium hydroxide. The mixture is heated to 95° C while being stirred magnetically. To the beaker then is added 13.7 parts of 4-sodiosulfobenzyl bromide and the temperature is maintained at 95° C for 3 hours. The viscous reaction solution then is added to 300 parts of water. The aqueous solution is concentrated to about one-tenth of its original volume and 250 parts of dimethyl sulfoxide added; isopropanol, about 200 parts, is then added resulting in a white, fluffy precipitate which is isolated by centrifugation. The solid is taken up in about 320 parts of an ethanol-methanol mixture, the volume reduced by about 25%, and isopropanol added. The product was isolated by centrifugation and dried at 60° C under reduced pressure. The product, 3-(p-sodiosulfobenzyloxy)-1,2-propanediol, is obtained in a yield of 3 parts and has the following analysis:

|  | % Carbon | % Hydrogen | % Sodium | % Sulfur |
|---|---|---|---|---|
| Calculated | 42.25 | 4.58 | 8.10 | 11.27 |
| Found | 40.60 | 4.20 | 8.05 | 12.40 |

EXAMPLE XI

The experiment of Example I is repeated, except that the p-phenolsulfonic acid sodium salt is replaced with 2240 parts of 2,5-dimethyl-4-phenolsulfonic acid sodium salt, to give 3-(2,5-dimethyl-4-sodiosulfophenoxy)-1,2-propanediol.

2,5-Dimethyl-4-phenolsulfonic acid is obtained by the sulfonation of 2,5-dimethylphenol {E. Wessely et al., Monatsh. Chem., 91, 57 (1960) [C.A., 54: 18412 (1960)]}. The sulfonation is accomplished in concentrated sulfuric acid at 80°-90° C; the resultant sulfonic acid is precipitated by diluting the reaction mixture with water and salting out the product with sodium chloride [M. E. Hultquist, et al., J. Am. Chem. Soc., 73,2558 (1951)]. Neutralization of the sulfonic acid with one mole of sodium hydroxide per mole of sulfonic acids affords the monosodium salt.

EXAMPLE XII

The experiment of Example I is repeated, except that the p-phenolsulfonic acid sodium salt is replaced with 2720 parts of 4'-hydroxy-4-biphenylsulfonic acid sodium salt, to give 3-(4-sodiosulfo-4'-biphenyloxy)-1,2-propanediol.

4'-Hydroxy-4-biphenylsulfonic acid is obtained by hydrolysis of the diazonium salt of 4'-amino-4-biphenylsulfonic acid; 4'-amino-4-biphenylsulfonic acid is obtained by the sulfonation of 4-aminobiphenyl at 90° in sulfuric acid{C. Finzi and G. Leandri, *Ann. Chim.*, 40, 334 (1950) [C.A. 45: 9010 (1951)]}.The sodium salt of the hydroxybiphenylsulfonic acid is obtained by neutralization of the free acid with one equivalent of sodium hydroxide.

EXAMPLE XIII

The experiment of Example I is repeated, except that the p-phenolsulfonic acid sodium salt is replaced with 2880 parts of 3-hydroxyphenyl 4-sodiosulfophenyl ether, to give 3-[3-(4-sodiosulfophenoxy)phenoxy]-1,2-propanediol.

3-Hydroxyphenyl 4-sodiosulfophenyl ether is obtained by neutralization of the free acid with one equivalent of sodium hydroxide. The free acid is obtained by the sulfonation of 3-phenoxyphenol, which in turn may be obtained by the fusion of resorcinol with sodium phenoxide (U.S. Pat. No. 2,516,931).

EXAMPLE XIV

To a 1-liter, three-necked flask, equipped with an addition funnel, mechanical stirrer, and reflux condenser fitted with a drying tube, is charged 200 parts of ethanol and 11.5 parts of sodium. When reaction is complete, 98 parts of p-phenolsulfonic acid, sodium salt and 0.5 part of potassium iodide are added. The mixture is stirred for 15 minutes at ambient temperature. To the flask then is added slowly 125 parts of diethyl bromomalonate and the mixture stirred for 10 hours at reflux. The reaction solution then is cooled and filtered. The filtrate is evaporated to dryness, the residue recrystallized from water, and then dried under reduced pressure. The product, dimethyl p-sodiosulfophenoxy)malonate, is obtained in a yield of 67 parts and has a sulfur content of 8.5% (theoretical, 8.8%).

EXAMPLE XV

A jacketed, steam-heated autoclave, fitted with an agitator and a packed distillation column with condenser, was charged with 2070 parts of dimethyl terephthalate, 1639 parts of ethylene glycol, 0.77 part of magnesium carbonate, and 0.44 part of sodium acetate. Over a period of about 200 minutes the mixture was heated to about 220° C and methanol distilled; at the end of this time methanol distillation was complete. The autoclave then was charged with 102 parts of adipic acid and 44 parts of 3-(4-sodiosulfophenoxy)-1,2-propanediol, both dissolved in 251 parts of ethylene glycol. The reaction mixture was refluxed for 20 minutes at a take-off ratio of 1:1, followed by refluxing for 20 minutes at total take-off. To the autoclave was added 1.32 parts of antimony trioxide, 3.3 parts of a 50% ethylene glycol solution of trimethylphosphite, and 1.76 parts of titanium dioxide. The resultant mixture then was transferred to a second jacketed autoclave, heated by means of a Dowtherm vapor system (heat transfer medium manufactured by Dow Chemical Co., Midland, Michigan) and fitted with an agitator, condenser, and means for operating the autoclave under reduced pressure. The mixture was polymerized over a period of 155 minutes under gradually decreasing pressure (to less than about 2.0mm mercury) and at a maximum polymerization temperature of 280° C. The resultant polymer was extruded and had an intrinsic viscosity of 0.57 deciliters/gram. As used herein, intrinsic viscosity is a measure of the degree of polymerization of the polyester and may be defined as:

$$\text{Limit } \frac{(\eta - \eta_0)}{\eta_0 C} \text{ as } C \text{ approaches } o$$

where $\eta$ is the viscosity of a dilute solution of the polyester in ortho-chlorophenol solvent, $\eta$ the viscosity of the pure solvent measured in the same units and at the same temperature as $\eta$, and c is the concentration in grams of polyester per 100 milliliters of solvent. Thus, intrinsic viscosity has the units, deciliters per gram. The polymer was spun and drawn to give a 150 denier filament yarn having a tenacity of 3.2 g.p.d. and an elongation of 24%. The yarn, white in color, was knitted into a hoseleg and dyed with Sevron Blue 5G. The hoseleg was dyed a medium shape of blue having good wash- and light-fastness properties.

Unless otherwise stated, all dyeings described herein use the following procedure: The scoured fabric is added to water (60:1 liquor ratio) containing 3 grams per liter of biphenyl and 10% (on the weight of fabric) of sodium sulfate decahydrate. The bath is heated at about 70° C for about 10 minutes and 2% (on the weight of fabric) of Sevron Blue 5G added. The bath is boiled for 90 minutes. The rinsed fabric then is scoured, rinsed, and dried.

As a control, poly(ethylene terephthalate) is prepared as described above, except that 2200 parts of dimethyl terephthalate is used and the ethylene glycol solution of 3-(4-sodiosulfophenoxy)-1,2-propanediol and adipic acid and sodium acetate are not added. The resultant polymer has an intrinsic viscosity of 0.61 deciliters per gram. The polymer is spun and drawn to give a 150 denier filament yarn having a tenacity of 4.2 g.p.d. and an elogation of 44%. The yarn is knitted into a hoseleg and dyed with 2% Sevron Blue 5G, as described above. Under these conditions, the control yarn absorbs none of the dye.

EXAMPLE XVI

In a manner similar to that of Example XV, a mixture of 2273 parts of dimethyl terephthalate, 1730 parts of ethylene glycol, 0.84 part of magnesium carbonate, and 0.48 part of lithium acetate is heated to about 220° C over a period of about 210 minutes; methanol is distilled. To the mixture then is added an ethylene glycol solution of 48 parts of 3-(4-lithiosulfophenoxy)-1,2-propanediol and 103 parts of adipic acid. The resultant mixture is refluxed for 20 minutes at a take-off ratio of 1:1, followed by refluxing for 20 minutes at total take-off. Titanium dioxide (8.38 parts), antimony trioxide (0.98 part), and trimethyl phosphite (3.59 parts of a 50% ethylene glycol solution) are added and the mixture is polymerized over a period of about 160 minutes under gradually decreasing pressure (to less than 3.0 mm mercury) and at a maximum polymerization temperature of 280° C. The resultant polymer is extruded and has an intrinsic viscosity of 0.67 deciliters/gram.

The polymer is spun and drawn to give a 160 denier filament yarn having a tenacity of 3.4 g.p.d. and an elognation of 34%. The yarn is knitted into a hoseleg and dyed to a medium shade of blue with 2% Sevron Blue 5G. The dyed hoseleg has good wash- and light-fastness properties. A control yarn made from unmodified poly(ethylene terephthalate) absorbs none of the dye.

EXAMPLE XVII

The experiment of Example XVI is repeated, except that the manganese acetate (1.40 parts), the amount of trimethyl phosphite (as a 50% ethylene glycol solution) is reduced to 2.40 parts, and the lithium acetate is replaced with lithium hydroxide monohydrate (1.40 parts). The resultant polymer has an intrinsic viscosity of 0.65 deciliters/gram.

The polymer is spun and drawn to give a 150 denier filament yarn having a tenacity 4.0 g.p.d. and an elogation of 44%. A knitted hoseleg and a control yarn are dyed with 2% Sevron Blue 5G with results similar to those described in Example XVI.

EXAMPLE XVIII

In a manner similar to that of Example XV, a mixture of 2400 parts of dimethyl terephthalate, 1730 parts of ethylene glycol, and 0.84 part of magnesium carbonate is heated to about 220° C over a period of about 170 minutes; methanol is distilled. To the mixture is added an ethylene glycol solution of 120 parts of 3-(4-sodiosulfophenoxy)-1,2-propanediol. The resultant mixture is refluxed for 30 minutes at a take-off ratio of 1:1. Antimony trioxide (0.96 part), trimethyl phosphite (2.40 parts of a 50% ethylene glycol solution), and titanium dioxide (8.38 parts) are added and the reaction mixture is polymerized over a period of about 205 minutes under gradually decreasing pressure (to less than 2.0mm mercury) and at a maximum polymerization temperature of 282° C. The resultant extruded polymer has an intrinsic viscosity of 0.51 deciliters/gram.

The polymer is spun and drawn to give a 150 denier filament yarn having a tenacity of 3.0 g.p.d. and an elongation of 27%. A knitted hoseleg and a control yarn are dyed with 2% Sevron Blue 5G with results similar to those described in Example XV.

EXAMPLE XIX

In a manner similar to that of Example XV, a mixture of 2400 parts of dimethyl terephthalate, 1730 parts of ethylene glycol, 0.84 part of magnesium carbonate, and 0.48 part of lithium acetate is heated to about 220° C over a period of about 165 minutes; methanol is distilled. To the mixture is added an ethylene glycol solution of 96 parts of 3-(4-lithiosulfophenoxy)-1,2-propanediol. The resultant mixture is refluxed for about 15 minutes at a take-off ratio of 1:1. Antimony trioxide (0.96 part), trimethyl phosphite (3.59 parts of a 50% ethylene glycol solution), and titanium dioxide (8.38 parts) are added and the reaction mixture is polymerized over a period of about 105 minutes under gradually decreasing pressure to about 3mm mercury or less) and at a maximum polymerization temperature of 287° C. The resultant polymer has an intrinsic viscosity of 0.68 deciliters/gram.

The polymer is spun and drawn to give a 160 denier filament yarn having a tenacity of 3.0 g.p.d. and an elongation of 21%. A knitted hoseleg and a control yarn are dyed with 2% Sevron Blue 5G with results similar to those described in Example XV.

EXAMPLE XX

In a manner similar to that of Example XV, a mixture of 1800 parts of dimethyl terephthalate, 1300 parts of ethylene glycol, and 0.63 part of magnesium carbonate is heated to about 220° C over a period of about 150 minutes; methanol is distilled. To the mixture is added an ethylene glycol solution of 72 parts of 3-(4-potassiosulfophenoxy) 1,2-propanediol, 0.72 part of antimony trioxide, and 1.80 parts of a 50% ethylene glycol solution of trimethyl phosphite. The mixture is polymerized over a period of about 115 minutes under gradually decreasing pressure (to about 0.2mm mercury) and at a maximum polymerization temperature of 280° C. The resultant polymer has an intrinsic viscosity of 0.47 deciliters/gram.

The polymer is spun and drawn to give a 65 denier filament yarn having a tenacity of 3.2 g.p.d. and an elongation of 7%. A knitted hoseleg and a control yarn are dyed with 2% Sevron Blue 5G with results similar to those described in Example XV.

EXAMPLE XXI

The experiment of Example XX is repeated, except that the amount of 3-(4-potassiosulfophenoxy)-1,2-propanediol is reduced to 36 parts and 81 parts of adipic acid is added. The resultant polymer has an intrinsic viscosity of 0.54 deciliters/gram.

The polymer is spun and drawn to give a 65 denier filament yarn having a tenacity of 3.3 g.p.d. and an elongation of 12%. A knitted hoseleg and a control yarn are dyed with 2% Sevron Blue 5G with results similar to those described in Example XX.

EXAMPLE XXII

In a manner similar to that of Example XV, a mixture of 2360 parts of dimethyl terephthalate, 1700 parts of ethylene glycol, and 1.48 parts of cobalt formate is heated to about 220° C over a period of about 180 minutes; methanol is distilled. To the mixture is added an ethylene glycol solution of 184 parts of isophthalic acid. The mixture is refluxed for about 60 minutes. An ethylene glycol solution of 84 parts of 3-(4-sodiosulfophenoxy)-1,2-propanediol, titanium dioxide (8.4 parts), 2.2 parts of a 50% solution of trimethyl phosphite in ethylene glycol, and antimony trioxide (1.4 parts) are then added and the resultant mixture is polymerized over a period of about 170 minutes under gradually decreasing pressure (to about 0.2mm mercury) and at a maximum polymerization temperature of 280° C. The resultant polymer has an intrinsic viscosity of 0.53 deciliters/gram.

The polymer is spun and drawn to give a 70 denier filament yarn. A knitted hoseleg and a control yarn are dyed with 2% Sevron Blue 5G with results similar to those described in Example XV.

EXAMPLE XXIII

In a manner similar to that of Example XV, a mixture of 2260 parts of dimethyl terephthalate, 1730 parts of ethylene glycol, and 1.51 parts of cobalt fomate is heated to about 220° C over a period of about 130 minutes; methanol is distilled. To the mixture is added an ethylene glycol solution of 138 parts of adipic acid. The mixture is refluxed at a take-off ratio of 1:1 for about 30 minutes. An ethylene glycol solution of 60 parts of 3-(7-sodiosulfo-2-naphthoxy)-1,2-propanediol, 4.02 parts of a 50% solution of trimethyl phosphite in ethylene glycol, and antimony trioxide (1.43 parts) are then added and the resultant mixture is polymerized over a period of about 150 minutes under gradually decreasing pressure (to less than 1.0mm mercury) and at a maximum polymerization temperature of 283° C. The extruded polymer has an intrinsic viscosity of 0.62 deciliters/gram.

The polymer is spun and drawn to give a 180 denier filament yarn having a tenacity of 3.2 g.p.d. and an elongation of 46%. A knitted hoseleg and a control yarn are dyed with 2% Sevron Blue 5G with results similar to those described in Example XV.

EXAMPLE XXIV

The experiment of Example XXIII is repeated, except that the amount of 3-(7-sodiosulfo-2-naphthoxy)-1,2-propanediol is reduced to 47.9 parts and 8.39 parts of titanium dioxide is added at the end of ester interchange. The resultant polymer has an intrinsic viscosity of 0.64 deciliters/gram.

The polymer is spun and drawn to give a 170 denier filament yarn having a tenacity of 3.5 g.p.d. and an elongation of 40%. A knitted hoseleg and a control yarn are dyed with 2% Sevron Blue 5G with results similar to those described in Example XXIII.

EXAMPLE XXV

The experiment of Example XX is repeated, except that the 3-(4-potassiosulfophenoxy)-1,2-propanediol is replaced with 72 parts of 3-(7-sodiosulfo-2-naphthoxy)-1,2-propanediol. The resultant polymer has an intrinsic viscosity of 0.51 deciliters/gram.

The polymer is spun and drawn to give a 70 denier filament yarn. A knitted hoseleg and a control yarn are dyed with 2% Sevron Blue 5G with results similar to those described in Example XX.

EXAMPLE XXVI

The experiment of Example XX is repeated, except that the 3-(4-potassiosulfophenoxy)-1,2-propanediol is replaced with 36 parts of 3-(5-sodiosulfo-1-naphthoxy)-1,2-propanediol and 108 parts of adipic acid (dissolved in ethylene glycol) is added at the end of ester interchange. The resultant polymer has an intrinsic viscosity of 0.55 deciliters/gram.

The polymer was spun and drawn to give a 70 denier filament yarn. A knitted hoseleg and a control yarn are dyed with 2% Sevron Blue 5G with results similar to those described in Example XX.

EXAMPLE XXVII

The experiment of Example XX is repeated, except that the 3-(4-potassiosulfophenoxy)-1,2-propanediol is replaced with 18 parts of 3-(4-lithiosulfophenoxy)-1,2-propanediol and 18 parts of 3-(5-sodiosulfo-1-naphthoxy)-1,2-propanediol, and 54 parts of adipic acid (dissolved in ethylene glycol) and 6.3 parts of titanium dioxide are added at the end of ester interchange. The resultant polymer has an intrinsic viscosity of 0.55 deciliters/gram.

The polymer is spun and drawn to give a 70 denier filament yarn. A knitted hoseleg and a control yarn are dyed with 2% Sevron Blue 5G with results similar to those described for Example XX.

EXAMPLE XXVIII

The experiment of Example XX is repeated, except that the amount of 3-(4-potassiosulfophenoxy)-1,2-propanediol is reduced to 18 parts and 18 parts of 3-(4-lithiosulfophenoxy)-1,2-propanediol is added. Also added are 81 parts of adipic acid and 1.44 parts of titanium dioxide. The resultant polymer has an intrinsic viscosity of 0.64 deciliters/gram.

The polymer is spun and drawn to give a 70 denier filament yarn. A knitted hoseleg and a control yarn are dyed with 2% Sevron Blue 5G with results similar to those described for Example XX.

EXAMPLE XXIX

The experiment of Example XX is repeated, except that the 3-(4-potassiosulfophenoxy)-1,2-propanediol is replaced with the lead salt of 3-(4-sulfophenoxy)-1,2-propanediol. Similar results are obtained.

EXAMPLE XXX

The experiment of Example XX is repeated, except that the 3-(4-potassiosulfophenoxy)-1,2-propanediol is replaced with the calcium salt of 3-(4-sulfophenoxy)-1,2-propanediol. Similar results are obtained.

EXAMPLE XXXI

The experiment of Example XX is repeated, except that the 3-(4-potassiosulfophenoxy)-1,2-propanediol is replaced with 3-(2,5-dimethyl-4-sodiosulfophenoxy)-1,2-propanediol. Similar results are obtained.

EXAMPLE XXXII

The experiment of Example XX is repeated, except that the 3-(4-potassiosulfophenoxy)-1,2-propanediol is replaced with 3-(4-sodiosulfo-4'-biphenyloxy)-1,2-propanediol. Similar results are obtained.

EXAMPLE XXXIII

The experiment of Example XX is repeated, except that the 3-(4-potassiosulfophenoxy)-1,2-propanediol is replaced with 3-[3-(4-sodiosulfophenoxylphenoxy]-1,2,propanediol. Similar results are obtained.

EXAMPLE XXXIV

The procedure of Example XVI is repeated, except that the autoclave charge consists of 2200 parts of dimethyl terephthalate, 1639 parts of ethylene glycol, 0.55 part of manganese acetate, 2.2 parts of cobalt formate, and 2.2 parts of lithium acetate, the 3-(4-lithiosulfophenoxy)-1,2-propanediol and adipic acid are reduced to 44 parts and 68 parts, respectively (both dissolved together in 186 parts of ethylene glycol), the titanium dioxide is reduced to 7.7 parts, the antimony trioxide is reduced to 0.87 part, and the trimethyl phosphite solution is reduced to 2.95 parts. The resultant polymer has an intrinsic viscosity of 0.57 deciliters per gram and is converted into 3.0 dpf by 1.5 inch staple having a tenacity of 3.4 grams per denier and an elongation of 45%. The tensile factor of the staple, (tenacity) (elongation)$^{1/2}$, is 23. Pack pressure rise during spinning averages 10 pounds per hour. Stable spinning, i.e. less than 0.05 breaks per pack per hour was evidenced over the entire period of the run, viz. 75 hours, and the filamentary material produced was characterized by 10.6% C.V.

EXAMPLE XXXV

The procedure of Example XXXIV is repeated, except that the lithium acetate is replaced with 2.9 parts of sodium acetate and the 3-(4-lithiosulfophenoxy)-1,2-propanediol is replaced with an equal amount of 3-(4-sodiosulfophenoxy)-1,2-propanediol. The resultant polymer has an intrinsic vicosity of 0.57 deciliters per gram and is converted into 3.0 dpf by 1.5 inch staple having a tenacity of 2.6 grams per denier and an elongation of 38%. The tensile factor of the staple is 16.0. Pack pressure rise during spinning averages 30 pounds per hour, a three-fold increase resulting from use of the sodium salt. The spun and drawn fiber has dispersed therein insoluble particles, illustrated by FIG. 1. The particles are absent when the lithium salt is employed (FIG. 2). Furthermore, spinning interruptions (such as breaks and discontinous filaments) are approximately twice as frequent and filament denier variance is about twice as great as a result of using the sodium salt.

What is claimed is:

1. The metallic salt of the structure

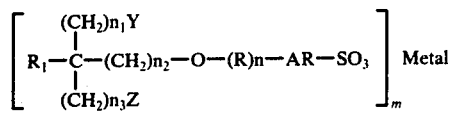

wherein $R_1$ represents either hydrogen or an alkyl radical containing from 1 to 6 carbon atoms; $n_1$, $n_2$, and $n_3$ each independently represent an integer from 0 to about 6 and $n_1 + n_2 + n_3$ is equal to or greater than 2 if Y and Z both are hydroxy; Y and Z are selected independently from the group consisting of hydroxy, carboxy and alkoxycarbonyl, the alkoxy portion of which contains from 1 to 6 carbon atoms; Ar represents an unsubstituted divalent aromatic hydrocarbon radical containing from 6 to about 12 carbon atoms; $m$ is an integer equal to the valency of the metal; R represents a divalent radical selected from the group consisting of alkylene and

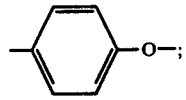

and $n$ is an integer, either 0 or 1, and when $n$ is 0, Metal is lithium.

2. The product of claim 1 wherein the anionic component of said metallic salt is an anion selected from the group consisting of:

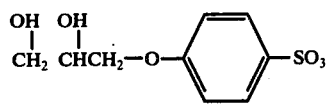

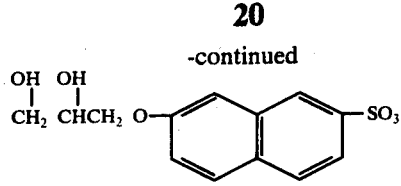

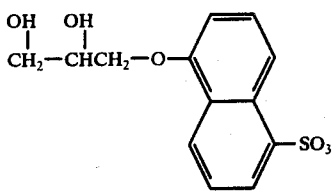

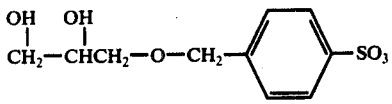

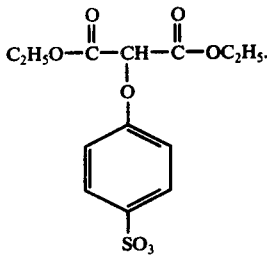

3. The product of claim 1 wherein the metallic component of said metallic salt is lithium.

4. The product of claim 1 wherein the metallic component of said metallic salt is sodium.

5. The metallic salt of the structure

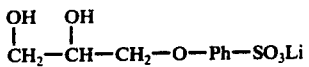

wherein Ph is unsubstituted phenylene.

6. An ester having the formula:

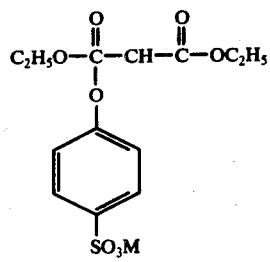

wherein M is lithium.

* * * * *